United States Patent
Killick et al.

(10) Patent No.: US 7,314,848 B1
(45) Date of Patent: Jan. 1, 2008

(54) ADJUVANT COMPOSITION FOR CHEMICALS USED IN AGRICULTURE

(75) Inventors: Robert W. Killick, Victoria (AU); Andrew R. Killick, Victoria (AU); Peter W. Jones, Victoria (AU); Peter R. Wrigley, Victoria (AU); John D. Morrison, Victoria (AU)

(73) Assignee: Victorian Chemicals International Pty Ltd., Victoria (AU)

( * ) Notice: Subject to any disclaimer, the term of this patent is extended or adjusted under 35 U.S.C. 154(b) by 0 days.

(21) Appl. No.: 09/831,301

(22) PCT Filed: May 5, 2000

(86) PCT No.: PCT/AU00/00416

§ 371 (c)(1),
(2), (4) Date: May 8, 2001

(87) PCT Pub. No.: WO00/67573

PCT Pub. Date: Nov. 16, 2000

(30) Foreign Application Priority Data

May 5, 1999 (AU) .................................. PQ 0175

(51) Int. Cl.
*A01N 25/00* (2006.01)
(52) U.S. Cl. ................................................... 504/116.1
(58) Field of Classification Search ............. 504/116.1
See application file for complete search history.

(56) References Cited

U.S. PATENT DOCUMENTS

| 4,175,572 A | * | 11/1979 | Hsiung et al. | ............... 132/204 |
| 4,964,874 A | * | 10/1990 | Saphakkul | ....................... 8/429 |
| 5,346,879 A | * | 9/1994 | Manabe et al. | .............. 504/115 |
| 5,436,225 A | * | 7/1995 | Hirabayashi et al. | ....... 504/289 |
| 5,672,564 A | | 9/1997 | Wigger et al. | ............... 504/116 |

FOREIGN PATENT DOCUMENTS

| EP | 0 358 494 | | 3/1990 |
| EP | 0 554 015 | | 8/1993 |
| EP | 0 598 404 | | 5/1994 |
| EP | 0 598 515 | | 5/1994 |
| FR | 2693738 | * | 1/1994 |
| JP | 50082105 | * | 7/1975 |
| JP | 5802389 | * | 2/1983 |
| WO | WO 90/07272 | | 7/1990 |
| WO | WO 97/00010 | | 3/1997 |
| WO | WO 98/17110 | | 4/1998 |
| WO | WO 99/51099 | | 10/1999 |

OTHER PUBLICATIONS

Tabbush et al., "Chemicals for the Forester: What About Additives?" Forestry and British Timber, Feb. 1998, pp. 12-13.
Turner, "Additives for Use with Herbicides, a Review," Malaysian Plan Protection Society, J. Pl. Prot. Troples 1(2):: pp. 77-86.
Turner et al., "Studies with Solubilized Herbicide Formulations," Proceedings 12th British Weed Control Conference, 1974, pp. 177-184.
Turner, Symposium on Application and Biology, "Studies with Alternative Glyphosate Formulations," 1985, pp. 135-145.
Turner, "Preliminary Results into Improving Herbicide Performance by the Use of Additives," 1975, pp. 82-90.

* cited by examiner

*Primary Examiner*—Alton Pryor
(74) *Attorney, Agent, or Firm*—Foley and Lardner LLP

(57) ABSTRACT

According to the invention an adjuvant for use with a chemical used in agriculture is provided comprising: (a) not in excess of about 75% by weight of one or more lipophilic solvents; (b) not in excess of about 50% by weight of one or more plant nutrients (e.g. ammonium salts of inorganic anions); and (c) not in excess of about 50% of a mixture of one or more cationic emulsifiers including surfactants which exhibit cationic characteristic in acidic conditions.

6 Claims, No Drawings

ADJUVANT COMPOSITION FOR CHEMICALS USED IN AGRICULTURE

FIELD OF THE INVENTION

The invention relates to an adjuvant for use with chemicals used in agriculture. More particularly, the adjuvant of the invention is particularly adapted for use with herbicides.

BACKGROUND OF THE INVENTION

In this specification, where a document, act or item of knowledge is referred to or discussed, this reference or discussion is not to be taken as an admission that the document, act or item of knowledge or any combination thereof was at the priority date:

(a) part of common general knowledge; or
(b) known to be relevant to an attempt to solve any problem with which this specification is concerned.

Whilst the following discussion highlights the invention with relation to herbicides, it is believed that the same principles apply to other chemicals used in agriculture, such as, plant hormones, insecticides, crop desiccants or crop defoliants.

Farmers rotate the use of their fields to allow the fields to regain their fertility. This means that at any one time there will be fields with crops and fields left bare. The bare fields are said to be fallow fields.

Weeds will still grow on the fallow fields, and while they will not be competing with a crop for nutrients or space, if they are left alone they will produce many seeds which will germinate and be a problem when the field is again used for crops. As a result, the farmer will spray the fallow fields with herbicide to kill the weeds. Since there is no crop on fallow fields, a non-selective herbicide can be used, such as glyphosate. Non-selective herbicides can also be used to control weeds in cropping situations where the crop has either been bred or genetically modified to be resistant to the herbicide.

There is a growing trend to produce adjuvants to improve the efficacy of agrochemicals, including herbicides. For example, in Australian patent application number 62833/98, an adjuvant for use with herbicides, crop defoliants and desiccants is disclosed including esters of fatty acids and nonionic emulsifiers.

Glyphosate is the most widely used non-selective herbicide for both fallow and cropping situations worldwide. Currently, a farmer may prepare the glyphosate spray with several additives to improve its efficacy. For example, it is known to add ammonium salts to improve the efficacy of glyphosate. The reasons for this improvement are not well understood and it is a complicated area of chemical and botanical reactions. However, it is believed that some anions can minimize the deleterious effect of hard water on herbicidal performance and the ammonium cation provides nutrition for the plant which enhances the uptake and translocation of the herbicide by the plant. Wetting agents are also used to improve leaf coverage. Petroleum fractions or other lipophilic materials (hereinafter referred to as lipophilic solvents) are used, especially in the summer months, to keep the herbicide in liquid form as the herbicide will be ineffective once it dries on the foliage.

The farmer may combine all these additives with the herbicide when the tank mix is prepared but the farmer may not know whether these components are compatible with each other. Some additives or adjuvants can actually antagonise each other and decrease the activity of the agrochemical. It is also inconvenient since there are several components which must be bought, measured and combined.

Farmers are always looking for more efficacious and convenient ways to enhance the performance of active ingredients. They would also prefer to simply add one composition which they know will enhance the efficacy of the herbicide rather than deal with several components where the resultant effect is unknown.

SUMMARY OF THE INVENTION

It was envisaged that incorporating ammonium salts into lipophilic solvent-based adjuvants would produce an adjuvant which provides active ingredient enhancement in several different ways. It was thought that the ammonium salts (a source of nitrogen) would enhance translocation through the fertilizer effects and could also increase leaf permeability, and the appropriate anion would reduce the effects of water hardness, whilst the lipophilic solvents would increase the availability of the active on the target and subsequently the absorption of the active into the target. However, preparing a stable homogeneous blend of lipophilic solvent with ammonium salts, particularly those which minimize the detrimental effects of hard water has not been easy to achieve because such salts are not soluble in lipophilic solvents. Hence, evaluating such a product as an adjuvant has not been possible.

It has been found that a homogeneous blend which is stable within normal storage conditions can be made which includes lipophilic solvents and lipophobic plant nutrients (such as ammonium salts) using cationic emulsifiers as a coupling agent.

According to the invention, a homogeneous liquid adjuvant for use with a chemical used in agriculture is provided comprising:

(a) not in excess of about 75% by weight of one or more lipophilic solvents;
(b) not in excess of about 50% by weight of one or more lipophobic plant nutrients (such as ammonium salts of inorganic anions); and
(c) not in excess of about 50% of a mixture of one or more cationic emulsifiers selected from the group consisting of cationic emulsifiers, emulsifiers having cationic characteristics in acidic conditions and mixtures thereof;

wherein the cationic emulsifier acts as a coupling agent between the lipophilic solvent and the lipophobic plant nutrient to form a homogeneous liquid composition.

Preferably, the adjuvant comprises:
(a) from 5 to 55% by weight of one or more lipophilic solvents;
(b) from 1 to 30% by weight of one or more lipophobic plant nutrients (such as ammonium salts of inorganic anions); and
(c) from 1 to 15% of a mixture of one or more cationic emulsifiers.

More preferably, the adjuvant comprises:
(a) from 15 to 35% by weight of one or more lipophilic solvents;
(b) from 5 to 25% by weight of one or more lipophobic plant nutrients (such as ammonium salts of inorganic anions); and
(c) from 1 to 10% of a mixture of one or more cationic emulsifiers.

The above proportions are based on the dry weight of the plant nutrients and cationic emulsifiers. It is common for these products to be supplied in aqueous or other diluted forms. It will be necessary to determine actual concentrations of these components prior to using these diluted products in a composition according to the invention.

The lipophilic solvents may be petroleum fractions, vegetable oils, synthetic triglycerides, alkyl esters of fatty acids, fatty alcohols, guerbet alcohols or any mixture thereof. Preferably, a petroleum fraction is used as it is more cost effective. More preferably, the petroleum fraction is a mineral oil. These mineral oils, for example, can be 70, 100 or 150 sec solvent neutral.

If alkyl esters of fatty acids are used then the alkyl moiety can be derived from the simple alcohols such as methyl-, ethyl-, butyl or propyl alcohols. There are innumerable variations of the esters of fatty acids which may be produced from the natural oils and fats such as lard, tallow and vegetable oils, such as canola, corn, sunflower and soyabean oils, or from specific blends produced by fatty acid manufacturers or from fatty acids produced by synthetic means.

The lipophobic plant nutrients include ammonium salts of inorganic anions (such as ammonium sulphate and phosphates) which are known to minimise the deleterious effects of hard water on herbicide performance. Preferably, the ammonium salt is ammonium sulphate. If an anhydrous ammonium salt is used then water may need to be added to the composition. However, if the ammonium salt is already in solution then additional water may not be necessary.

The term "cationic emulsifiers" is used to include emulsifiers which are commonly classified as cationic as well as those which exhibit cationic properties in acidic conditions. An example of an emulsifier which is commonly classified as cationic is a quaternary cationic emulsifier. Examples of emulsifiers which exhibit cationic properties in acidic conditions are fatty amines, amine oxides and amine ethoxylates. Amphoteric emulsifiers such as betaines may also exhibit such properties.

Preferably, the cationic emulsifiers are selected from dimethylcocoamine, dimethyl-laurylamine oxide, alkyltrimethylammonium chloride, alkyl dimethylbenzylammonium chloride, alkylpyridium chloride, alkylimidazolium chloride, or mixtures thereof. More preferably, the cationic emulsifier is selected from alkyltrimethylammonium chloride, dimethyl lauryl amine oxide or mixtures thereof.

Preferably, the adjuvant composition comprises other components to improve the form of the composition. These other components may be added to form a micro-emulsion. The other components may be selected from the group consisting of nonionic emulsifiers, co-solvents and mixtures thereof.

Preferably, the nonionic emulsifiers are alkyl polysaccharides, sorbate emulsifiers, alkyl bearing ethoxylates or fatty alkanolamides. Alkyl polysaccharides are sometimes called alkyl polyglucosides, alkyl glucosides or alkyl saccharides. The sorbate emulsifiers are sorbitan mono- (or sesqui-) esters of fatty acids and include sorbitan mono-oleate and sorbitan monolaurate. Preferably, the sorbate emulsifier is sorbitan mono-oleate. An example of a fatty alkanolamide is oleyldiethanolamide. The co-solvents include propylene glycol, 1,3-butanediol, hexylene glycol, polypropylene glycols and ethanol. Anionic emulsifiers may be added when compatible with the other components.

When mineral oils are used as the lipophilic solvent and ammonium sulphate is used as the plant nutrient, preferably, the composition comprises a cationic emulsifier, the following nonionic emulsifiers: alkylpolysaccharides, fatty alkanolamide and sorbitan mono-oleate or alcohol ethoxylate, as well as the following co-solvents: 1,3-butanediol and ethanol.

When esters of fatty acids are used as the lipophilic solvent, preferably, a mixture of at least two cationic emulsifiers are used. One of the cationic emulsifiers may be an amphoteric emulsifier acting as a cationic emulsifier. More preferably, the mixture of cationic emulsifiers comprises fatty quaternary ammonium chlorides or fatty amine oxides in conjunction with fatty alkyldimethylamine salts of simple organic acids. For example, the fatty alkyldimethylamine salts of simple organic acids could be cocodimethylamine or lauryldimethylamine with citric acid. Other simple organic acids include acetic, 2-ethylhexanoic acid, tartaric, maleic and lactic acid.

In another preferred form of the invention, the adjuvant for use with a chemical used in agriculture further comprises one or more other available adjuvant components. The adjuvant component may be selected from pH modifiers, spray drift retardants, stickers, rainfasteners and wetters.

According to another embodiment of the invention, there is provided an agrochemical composition comprising a chemical used in agriculture and an activity enhancing amount of a homogeneous liquid adjuvant, said homogeneous liquid adjuvant comprising:

(a) not in excess of about 75% by weight of one or more lipophilic solvents;

(b) not in excess of about 50% by weight of one or more lipophobic plant nutrients (such as ammonium salts of inorganic anions); and (c) not in excess of about 50% of a mixture of one or more cationic emulsifiers selected from the group consisting of cationic emulsifiers, emulsifiers which exhibit cationic characteristics in acidic conditions and mixtures thereof;

wherein the cationic emulsifier acts as a coupling agent between the lipophilic solvent and the lipophobic plant nutrient to form a homogeneous liquid composition.

According to a further embodiment of the invention, there is provided a homogeneous liquid adjuvant when used with a chemical used in agriculture comprising:

(a) not in excess of about 75% by weight of one or more lipophilic solvents;

(b) not in excess of about 50% by weight of one or more lipophobic plant nutrients (such as ammonium salts of inorganic anions); and (c) not in excess of about 50% of a mixture of one or more cationic emulsifiers selected from the group consisting of cationic emulsifiers, emulsifiers which exhibit cationic characteristics in acidic conditions and mixtures thereof;

wherein the cationic emulsifier acts as a coupling agent between the lipophilic solvent and the lipophobic plant nutrient to form a homogeneous liquid composition.

According to an even further embodiment of the invention, there is provided a method for enhancing the activity of a chemical used in agriculture comprising the step of combining the chemical with a homogeneous liquid adjuvant comprising:

(a) not in excess of about 75% by weight of one or more lipophilic solvents;

(b) not in excess of about 50% by weight of one or more lipophobic plant nutrients (such as ammonium salts of inorganic anions); and (c) not in excess of about 50% of a mixture of one or more cationic emulsifiers selected from the group consisting of cationic emulsifiers, emulsifiers which exhibit cationic characteristics in acidic conditions and mixtures thereof;

wherein the cationic emulsifier acts as a coupling agent between the lipophilic solvent and the lipophobic plant nutrient to form a homogeneous liquid composition.

According to another embodiment of the invention, there is provided a method of treating vegetation comprising the step of applying an agrochemical composition comprising a chemical used in agriculture and a homogeneous liquid adjuvant comprising:
(a) not in excess of about 75% by weight of one or more lipophilic solvents;
(b) not in excess of about 50% by weight of one or more lipophobic plant nutrients (such as ammonium salts of inorganic anions); and
(c) not in excess of about 50% of a mixture of one or more cationic emulsifiers selected from the group consisting of cationic emulsifiers, emulsifiers which exhibit cationic characteristics in acidic conditions and mixtures thereof;

wherein the cationic emulsifier acts as a coupling agent between the lipophilic solvent and the lipophobic plant nutrient to form a homogeneous liquid composition.

EXAMPLES

The invention will now be further explained and illustrated by the following non-limiting examples.

Lipophilic Solvents, Cationic Emulsifiers, Plant Nutrients and Other Components Used

| | |
|---|---|
| 1,3 Butanediol | ex Hoechst Celanese, USA |
| '880' ammonia | ex Orica, Australia |
| Acetic acid glacial | ex Orica, Australia |
| Algene SC25 | 25% paste of stearyldimethylbenzyl ammonium chloride ex ICI Ltd, UK |
| Alkadet 15 | 70% solution of alkyl polysaccharide ex Huntsman Corporation, Australia |
| Ammonium nitrate | >99% purity ex Orica, Australia |
| Ammonium sulphate | >99% purity ex Redox, Australia |
| BS 1000 | commercial adjuvant containing alcohol alkoxylate ex Cropcare, Australia |
| Cation BB | lauryltrimethyl ammonium chloride in a 30% solution containing salt ex AMTRADE Australia |
| Citric acid | ex Citrique Belge, Belgium |
| Dimethyl cocoamine | ex Proctor & Gamble, USA |
| Dimethyl laurylamine | ex Fina Chemicals, Belgium |
| Empigen BB | 28% solution of cocobetaine ex Albright and Wilson, Australia |
| Ethanol | ex CSR, Australia and contains 2-3% methanol. |
| Ethyl oleate | ex Victorian Chemical Company, Australia and contains approximately 80% w/w ethyl and 20% w/w methyl esters of canola oil. |
| Glyphosate CT solution | commercial herbicide containing 450 g/L glyphosate ex Nufarm, Austrtalia |
| HASTEN | commercial adjuvant containing 704 g/l ethyl oleate ex Victorian Chemical Company, Australia |
| Lactic acid | 88% solution ex Musashima, Japan |
| Liase | commercial adjuvant containing 417 g/l ammonium sulphate ex Nufarm, Australia |
| LI700 | commercial adjuvant containing 345 g/l phospholipids and 355 g/l proprionic acid ex Nufarm, Australia |
| Lorol C1298 | Laurylalcohol ex Henkel, Australia |
| Oleylamine | ex Fina Chemicals, Belgium |
| Oxamin LO | 30% solution of lauryldimethylamine oxide ex Huntsman Corporation, Australia |
| Potassium ammonium phosphate | 46% aqueous solution ex Wilbur Ellis Company, USA |
| Propylene glycol | industrial grade ex Dow Chemicals, Australia |
| Prorex 36 | 100 sec solvent neutral mineral oil ex Mobil, Australia |
| Quatramine C16/29 | 29% solution of cetyltrimethyl-ammonium chloride ex APS Chemicals, Australia |
| Quatramine NC50 | 50% solution of alkyldimethylbenzyl ammonium chloride ex APS Chemicals, Australia |
| Radiaquat 6465 | 30% solution of lauryl trimethyl ammonium chloride ex Fina Chemicals, Belgium |
| Roundup CT Xtra | commercial herbicide containing 490 g/L glyphosate ex Monsanto, Australia |
| Shell P830 | paraffinic 70 sec oil ex Shell, Australia |
| Span 80 | sorbitan mono-oleate ex Huntsman Corporation, Australia |
| Teric N2 | nonylphenol 2 moles ethylene oxide ex Huntsman Corporation, Australia |
| Teric N9 | nonylphenol 9 moles ethylene oxide ex Huntsman Corporation, Australia |
| Terwet 3001 | 70% solution of alkyl polysaccharide ex Huntsman Corporation, Australia |
| Tridecanol | ex Shell Chemicals, Australia |
| Urea | ex Orica, Australia |
| Vicamid 825 | oleyldiethanolamide ex Victorian Chemical Company, Australia |
| VOC RHT 100 | paraffinic 100 sec oil ex Safety Kleen, USA |
| Winter Oil | commercial adjuvant containing emulsified mineral oil ex BP, Australia |

Example 1

In this example, low levels of glyphosate were used to treat a broadleaf weed and a grass weed.

Adjuvant Compositions Tested

The following adjuvant formulations were prepared and are stable compositions. A formulation was classified as stable if it remained a clear liquid without detectable phase separation for at least 48 hours through the temperature range 0 to 40° C. Adjuvant D which is an oil-in-water emulsion was only tested at room temperature.

The proportions are shown as percentage by weight.

| | lipophilic solvent | | plant nutrient | | | | | cationic emulsifier | other components | | |
|---|---|---|---|---|---|---|---|---|---|---|---|
| Adjuvant | Ethyl oleate | Prorex 36 | Ammonium nitrate | Ammonium sulfate | Potassium ammonium phosphate | Urea | Added Water | Radiaquat 6465 | Alkadet 15 | Ethanol | Span 80 |
| A | — | 28 | 16 | — | — | 12 | 16 | 12 | 3 | 3 | 10 |
| B | — | 22 | — | 17 | — | — | 39 | 11 | 4 | — | 7 |

-continued

| Adjuvant | lipophilic solvent | | Ammonium nitrate | Ammonium sulfate | plant nutrient Potassium ammonium phosphate | Urea | Added Water | cationic emulsifier Radiaquat 6465 | other components | | |
|---|---|---|---|---|---|---|---|---|---|---|---|
| | Ethyl oleate | Prorex 36 | | | | | | | Alkadet 15 | Ethanol | Span 80 |
| C | — | 26 | — | — | 50 | — | — | 10 | 7 | — | 7 |
| D | 25 | — | — | — | 47 | — | 6 | 9 | 6 | — | 6 |

Note that there was no water added to Adjuvant C but there was a water content of about 30%.

The above adjuvants were tested by combining the adjuvant with Glyphosate CT in a water-based tank mix. Compositions 2 to 14 below are spray tank mixtures containing glyphosate and other components as listed.

The spray tank mixture was applied to the plants at a rate equivalent to 64 liters/hectare. The glyphosate used was the commercially available Glyphosate CT at a rate equivalent to either 60 g a.i/hectare or 120 g a.i/hectare which is 12.5% and 25% respectively of the normal application rate. The adjuvants were added volumetrically to the tank mix as a percentage of the tank mix volume.

Compositions Tested.

| Composition | Other Components |
|---|---|
| 1. | unsprayed control |
| 2. | no other components |
| 3. | 0.2% BS 1000 |
| 4. | 1.0% Winter Oil |
| 5. | 2.0% Liase |
| 6. | 0.2% BS 1000, 1.0% Winter Oil and 2.0% Liase |
| 7. | 0.75% of Adjuvant A |
| 8. | 1.5% of Adjuvant A |
| 9. | 0.75% of Adjuvant B |
| 10. | 1.5% of Adjuvant B |
| 11. | 0.75% of Adjuvant C |
| 12. | 1.5% of Adjuvant C |
| 13. | 0.75% of Adjuvant D |
| 14. | 1.5% of Adjuvant D |

Spiny Emex

The above compositions were tested on spiny emex shoots which is a broad leaf weed. The level of effectiveness of each composition was determined using the fresh weight of the weed 31 days after the spray application. The results are an average of seven replicates.

The lower the fresh weight of the weed the more effective the composition.

Test Results with Spiny Emex Shoots

| Composition | Fresh weight (g) | |
|---|---|---|
| | (60 g/ha glyphosate) | (120 g/ha glyphosate) |
| 1. (control) | 15.1 | 15.1 |
| 2. | 14.0 | 9.8 |
| 3. | 13.2 | 8.5 |
| 4. | 12.1 | 7.1 |
| 5. | 11.0 | 6.5 |
| 6. | 13.0 | 8.8 |
| 7. | 12.2 | 5.3 |
| 8. | 10.8 | 5.0 |

-continued

| Composition | Fresh weight (g) | |
|---|---|---|
| | (60 g/ha glyphosate) | (120 g/ha glyphosate) |
| 9. | 7.9 | 4.0 |
| 10. | 6.1 | 3.5 |
| 11. | 10.8 | 6.8 |
| 12. | 6.9 | 4.2 |
| 13. | 9.2 | 3.0 |
| 14. | 5.5 | 3.6 |

Analysis

These results illustrate that when using low levels of glyphosate on a broadleaf weed, Compositions 7 to 14 are more efficient than Composition 2 which is glyphosate alone therefore Adjuvants A to D are acting as adjuvants. At 120 g/ha, Compositions 7 to 14 are significantly better than Composition 2. At 60 g/ha, the effectiveness of Compositions 7 to 14 depended on the amount of adjuvant used and the composition of the adjuvant. Adjuvants B and D had superior results at both concentrations.

Compositions 7 to 14 compared favorably to Compositions 3 to 6 which contain commercially available adjuvants. At 120 g/ha, Compositions 7 to 10 and 12 to 14 had superior results to Compositions 3 to 6. At 60 g/ha, depended on the adjuvant used and the amount of adjuvant used. Adjuvants B and D had superior results at both concentrations.

Compositions 7 to 14 are also more efficient than the mere combination of additives in Composition 6. Therefore, the invention provides an adjuvant for a herbicide in a single homogeneous composition which is more effective than the mixture which a farmer would obtain if the commonly used additives were simply mixed together in the tank mix.

Ryegrass

The above compositions were tested on ryegrass shoots which is a grass. The fresh weight (grams) of the weeds were measured 19 days after the spray application. The results are an average of eight replicates.

Test Results for Ryegrass Shoots

| Composition | Fresh weight (g) | |
|---|---|---|
| | (60 g/ha glyphosate) | (120 g/ha glyphosate) |
| 1. | 4.0 | 4.0 |
| 2. | 3.0 | 2.0 |
| 3. | 3.75 | 0.75 |
| 4. | 3.5 | 0.75 |
| 5. | 2.0 | 1.0 |
| 6. | 2.0 | 1.0 |

-continued

| Composition | Fresh weight (g) | |
|---|---|---|
| | (60 g/ha glyphosate) | (120 g/ha glyphosate) |
| 7. | 3.5 | 1.5 |
| 8. | 2.75 | 1.0 |
| 9. | 1.75 | 0.5 |
| 10. | 1.25 | 0.25 |
| 11. | 1.75 | 0.5 |
| 12. | 1.75 | 0.25 |
| 13. | 2.25 | 0.25 |
| 14. | 1.25 | 0.25 |

Analysis

These results illustrate that Compositions 9 to 14 are clearly more efficient than Composition 2 which is glyphosate alone and thus that Adjuvants B, C and D are acting as adjuvants.

Compositions 9 to 14 compared favorably to Compositions 3 to 6. The results depended on the adjuvant used and the amount of adjuvant used.

At the lowest glyphosate level (60 g/ha) the best results were achieved with Adjuvants B and D at the higher rates (Compositions 10 and 14). These compositions are clearly more efficient than Compositions 3 to 6.

At the higher glyphosate level (120 g/ha). Compositions 9 to 14 are clearly more efficient than Compositions 3 to 6. Adjuvants B, C and D had superior results.

Adjuvant A (represented by Compositions 7 and 8) was less effective on ryegrass shoots at the lower glyphosate level but of comparable performance as Compositions 5 and 6 at the higher glyphosate level.

Example 2

In this example, the effect of external conditions and hard water are tested. Hard water has been shown to reduce the efficacy of glyphosate. Higher temperatures increase the evaporation rate of the spray water and thereby can leave the glyphosate dry on the foliage rendering it less available for absorption into the plant.

Water hardness is measured in World Health Organisation units of hardness (WHO). One WHO is equivalent to 343 ppm of $CaCO_3$.

The test compositions were tested on ryegrass using water of three differing degrees of hardness: Melbourne tap water (typically 20 ppm), 1WHO and 3WHO water. The fresh weight (grams) of the weeds were measured 19 days after spray application. The results are an average of seven or eight replicates.

The test compositions were tested on ryegrass exposed to two differing environmental temperature conditions (Standard and Hot) for one hour before and two hours after spraying. Standard temperature was that of the controlled greenhouse (approximately 20° C.) whereas Hot temperature was induced in a 30° C. constant environment room. The fresh weight of the weeds was measured 21 days after spraying. The results are an average of eight replicates.

The following adjuvants are stable compositions and were tested in Example 2.

| Component | | Adjuvant E | Adjuvant F |
|---|---|---|---|
| Lipophilic solvent | Prorex 36 | 22 | 21 |
| Plant nutrient | Ammonium Sulphate | 15 | 14 |
| | Water | 30 | 30 |
| Cationic Emulsifier | Quatramine C16/19 | 12 | 7 |
| | Algene SC25 | — | 7 |
| Other Components | 1,3 Butanediol | 4 | 4 |
| | Ethanol | 2 | 2 |
| | Span 80 | 6 | 6 |
| | Terwet 3001 | 6 | 6 |
| | Vicamid 825 | 3 | 3 |

The above adjuvants were tested by combining the adjuvant with Glyphosate CT in a water-based tank mix. Compositions 16 to 23 are spray tank mixtures containing glyphosate and other components as listed.

The glyphosate was applied at 120 g ai/ha (25% of the normal application rate).

| Composition | Other Components |
|---|---|
| 15. | unsprayed control |
| 16. | no other components |
| 17. | 0.25% LI700 |
| 18. | 0.25% Adjuvant E |
| 19. | 1.0% Adjuvant E |
| 20. | 0.25% Adjuvant F |
| 21. | 0.1% BS 1000 and 2.0% Liase |
| 22. | 0.25% HASTEN |
| 23. | Roundup CT Xtra (used in place of Glyphosate CT to provide an equivalent amount of glyphosate) |

Test Results for Ryegrass Shoots

| Composition | Tap/Standard | 1WHO | 3WHO | Hot |
|---|---|---|---|---|
| 15. | 1.726 | 1.726 | 1.726 | 1.726 |
| 16. | 0.292 | 0.871 | 1.696 | 0.455 |
| 17. | 0.401 | 0.487 | 1.185 | 0.647 |
| 18. | 0.139 | 0.364 | 1.571 | 0.315 |
| 19. | 0.157 | 0.184 | 0.312 | 0.173 |
| 20. | 0.199 | 0.425 | 1.057 | 0.315 |
| 21. | 0.127 | 0.130 | 0.158 | 0.266 |
| 22. | 0.186 | 0.325 | 1.588 | 0.223 |
| 23. | 0.264 | 0.534 | 1.684 | 0.293 |

Effect of Water Hardness

The results for Compositions 16 and 23 clearly indicate that hard water reduces the efficacy of glyphosate. Composition 21 illustrates that the use of ammonium sulphate improves the performance of glyphosate in hard water. Composition 19 which contains an adjuvant according to the invention achieved excellent results in all of the conditions. Compositions 18 and 20 illustrate that to achieve the suitable results a sufficient amount of adjuvant must be used such as that in Composition 19.

Adjuvant E (in Composition 19) is clearly effective as an adjuvant for reduced levels of glyphosate on ryegrass in the presence of hard water. As with Liase and other ammonium sulphate bearing adjuvants, the amount of Adjuvant E must be adjusted to meet the degree of water hardness.

Effect of Temperature Conditions

The performance of glyphosate is clearly reduced in Hot conditions. Compositions 18 and 20 contained 0.25% of an adjuvant according to the present invention and achieved comparable results to the known additives. Composition 19 which contained 1.0% of an adjuvant according to the invention continued to perform well under Hot conditions. Under Hot conditions, Composition 19 actually performed as well as compositions with known additives under Standard conditions.

The Hot conditions resulted in higher fresh weights. Composition 19 clearly resisted this decrease in performance in a satisfactory manner. Adjuvant E (in Compositions 18 and 19) is clearly effective as an adjuvant for reduced levels of glyphosate on ryegrass in Hot conditions when used in appropriate amounts.

Example 3

This example investigated the formulation stability when another typical adjuvant component is added. The additional component tested was BIVERT concentrate which is the active ingredient of BIVERT, a spray drift retardant ex Wilbur-Ellis Company.

The following compositions were prepared as homogeneous blends. All proportions are by weight. All the ingredients except for the citric acid were stirred together. Then enough citric acid was then added with stirring to clear the mixture and give high temperature stability.

Each of the adjuvants G, H and I were found to be homogeneous blends which remained clear without phase separation for at least 48 hours through the temperature range 0 to 40° C.

Adjuvant Compositions with Spray Drift Retardant

|  |  | Adjuvant | | |
|---|---|---|---|---|
| Component |  | G | H | I |
| Lipophilic solvent | Ethyl oleate | 30 | 30 | 30 |
| Plant nutrient | Ammonium sulphate | — | — | 10 |
|  | Potassium ammonium phosphate | 20 | 20 | — |
|  | Water | 10 | 10 | 20 |
| Cationic Emulsifier | Dimethyl laurylamine | 10 | 10 | 10 |
|  | Quatramine C16/29 | — | 6 | 6 |
|  | Radiaquat 6465 | 5 | — | — |
| Other Components | Alkadet 15 | 5 | 5 | 5 |
|  | BIVERT concentrate | 10 | 10 | 10 |
|  | Citric acid | 2 | 2 | 2 |
|  | Propylene Glycol | 5 | 3 | 3 |
|  | Vicamid 825 | 5 | 4 | 4 |

Example 4

A series of formulations were developed to test their stability. It was found that each of the following formulations are stable compositions or semi-stable emulsions at ambient temperature. All proportions are by weight.

| Adjuvant | J | K | L | M | N | O | P | Q | R | S | T | U | V | W | X | Y |
|---|---|---|---|---|---|---|---|---|---|---|---|---|---|---|---|---|
| Other components | | | | | | | | | | | | | | | | |
| Vicamid 825 | — | — | — | — | — | — | — | 11.5 | 9 | 7.5 | 90 | 2 | 2 | 2 | 11 | 12 |
| Terwet 3001 | — | — | — | — | — | — | — | — | — | — | 70 | — | — | — | 22 | 25 |
| Teric N9 | — | — | — | — | — | — | — | — | — | — | 25 | — | — | — | — | — |
| Span 80 | 7 | — | — | — | — | — | — | — | — | — | — | 11 | 10 | 10 | 22 | 23 |
| Propylene glycol | — | — | — | — | — | — | — | 7 | 10 | — | — | — | — | — | — | — |
| Oleylamine | — | — | — | — | — | 5 | — | — | — | — | — | — | — | — | — | — |
| Lactic acid | — | — | 1 | — | 3 | — | — | — | — | — | — | — | — | — | — | — |
| Ethanol | — | — | — | — | — | — | — | — | — | — | 25 | — | — | — | 6 | 4 |
| Citric acid | — | — | — | 1 | — | — | — | 2.5 | 1-1.5 | 1-1.5 | — | — | — | — | — | 4 |
| Alkadet 15 | 4 | — | — | — | — | — | — | 5 | 5 | 5 | — | 6 | 7 | 7 | — | — |
| Acetic Acid | — | — | — | — | 1 | — | — | — | — | — | — | — | — | — | — | — |
| '880' ammonia | — | — | — | — | — | — | — | — | — | — | 5 | — | — | — | — | — |
| 1,3 butanediol | — | — | — | — | — | — | — | — | 5 | 40 | 1 | 1 | 2.5 | 15 | 15 |  |
| Cationic emulsifier | | | | | | | | | | | | | | | | |
| Radiaquat 6465 | 11 | — | — | — | 10 | — | — | — | — | — | — | — | — | — | — | — |
| Quatramine NC50 | — | — | — | — | — | 15 | — | — | — | — | — | — | — | — | — | — |
| Quatramine C16/29 | — | — | — | — | — | — | — | — | 10 | 10 | 130 | — | — | — | — | — |
| Oxamin LO | — | — | — | — | — | — | — | — | — | — | — | — | — | — | 71 | 70 |
| Empigen BB | — | — | — | — | — | — | — | 10 | 10 | 10 | — | — | — | — | — | — |
| Dimethyl laurylamine | — | — | — | — | 10 | — | — | 10 | — | — | — | — | — | — | — | — |
| Dimethyl cocoamine | — | — | 10 | 10 | — | — | — | — | — | — | 5 | — | — | — | — | — |
| Cation BB | — | — | — | — | — | — | 15 | — | — | — | — | 16 | 14 | 15 | — | — |
| Algene SC25 | — | 20 | — | — | — | — | — | — | — | — | — | — | — | — | — | — |
| Plant nutrient | | | | | | | | | | | | | | | | |
| Added Water | 38 | 30 | 30 | 30 | 40 | 30 | 50 | 20 | 20 | 20 | 200 | 58 | 43 | 57 | 121 | 81 |
| Urea | — | — | — | — | — | — | — | — | — | — | 100 | — | — | — | — | — |
| Ammonium sulfate | 17 | 10 | 10 | 10 | 10 | 15 | 10 | 10 | 10 | 10 | — | 25 | 20 | 24 | 55 | 60 |
| Ammonium nitrate | — | — | — | — | — | — | — | — | — | — | 100 | — | — | — | — | — |
| Lipophilic solvent | | | | | | | | | | | | | | | | |
| VOC RHT 100 | — | — | — | — | — | — | — | — | — | — | — | — | — | 37 | — | — |

-continued

| Adjuvant | J | K | L | M | N | O | P | Q | R | S | T | U | V | W | X | Y |
|---|---|---|---|---|---|---|---|---|---|---|---|---|---|---|---|---|
| Tridecanol | — | — | — | — | — | — | 10 | — | — | — | — | — | — | — | — | — |
| Shell P830 | — | — | — | — | — | — | — | — | — | — | — | — | 43 | — | — | — |
| Prorex 36 | 22 | 38 | — | 50 | 60 | — | — | — | — | — | — | 34 | — | — | 77 | 80 |
| LOROL C1298 | — | 2 | — | — | — | — | 15 | — | — | — | — | — | — | — | — | — |
| Ethyl oleate | — | — | 50 | — | — | 35 | — | 30 | 30 | 30 | 240 | — | — | — | — | — |

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A homogeneous liquid adjuvant for use with a chemical used in agriculture comprising:
   from 15 to 35% by weight of one or more mineral oils;
   from 5 to 25% by weight of one or more ammonium salts of inorganic anions selected from ammonium sulfate, ammonium phosphate and mixtures thereof; and
   from 1 to 10% of one or more cationic emulsifiers selected from the group consisting of fatty quaternary ammonium chlorides, fatty amine oxides, fatty alkyldimethylamine salts of simple organic acids and mixtures thereof;
   wherein the cationic emulsifier acts as a coupling agent between the mineral oils and the ammonium salts to form a homogeneous liquid composition.

2. A homogeneous liquid adjuvant for use with a chemical used in agriculture comprising:
   from 15 to 35% by weight of one or more mineral oils;
   from 5 to 25% by weight of one or more ammonium salts of inorganic anions selected from ammonium sulfate, ammonium phosphate and mixtures thereof;
   from 1 to 10% of one or more cationic emulsifiers selected from the group consisting of fatty quaternary ammonium chlorides, fatty amine oxides, fatty alkyldimethylamine salts of simple organic acids and mixtures thereof; and
   from 1 to 30% of one or more other components to improve the form of the composition selected from nonionic emulsifiers, co-solvents and mixtures thereof;
   wherein the cationic emulsifier acts as a coupling agent between the mineral oils and the ammonium salts to form a homogeneous liquid composition.

3. A homogeneous liquid adjuvant for use with a chemical used in agriculture comprising:
   from 15 to 35% by weight of one or more mineral oils;
   from 5 to 25% by weight of one or more ammonium salts of inorganic anions selected from ammonium sulfate, ammonium phosphate and mixtures thereof;
   from 1 to 10% of one or more cationic emulsifiers selected from the group consisting of fatty quaternary ammonium chlorides, fatty amine oxides, fatty alkyldimethylamine salts of simple organic acids and mixtures thereof; and
   from 1 to 30% of one or more other components to improve the form of the composition selected from alkyl polysaccharides, sorbate emulsifiers, fatty alkanolamides, glycols and mixtures thereof;
   wherein the cationic emulsifier acts as a coupling agent between the mineral oils and the ammonium salts to form a homogeneous liquid composition.

4. A homogeneous liquid adjuvant for use with a chemical used in agriculture comprising:
   from 15 to 35% by weight of one or more alkyl esters of fatty acids;
   from 5 to 25% by weight of one or more ammonium salts of inorganic anions selected from ammonium sulfate, ammonium phosphate and mixtures thereof; and
   from 1 to 10% of a mixture of two or more cationic emulsifiers selected from the group consisting of fatty quaternary ammonium chlorides, fatty amine oxides, fatty alkyldimethylamine salts of simple organic acids and mixtures thereof;
   wherein the cationic emulsifier acts as a coupling agent between the alkyl esters of fatty acids and the ammonium salts to form a homogeneous liquid composition.

5. A homogeneous liquid adjuvant for use with a chemical used in agriculture comprising:
   from 15 to 35% by weight of one or more alkyl esters of fatty acids;
   from 5 to 25% by weight of one or more ammonium salts of inorganic anions selected from ammonium sulfate, ammonium phosphate and mixtures thereof;
   from 1 to 10% of a mixture of two or more cationic emulsifiers selected from the group consisting of fatty quaternary ammonium chlorides, fatty amine oxides, fatty alkyldimethylamine salts of simple organic acids and mixtures thereof; and
   from 1 to 30% of one or more other components to improve the form of the composition selected from nonionic emulsifiers, co-solvents and mixtures thereof;
   wherein the cationic emulsifier acts as a coupling agent between the alkyl esters of fatty acids and the ammonium salts to form a homogeneous liquid composition.

6. A homogeneous liquid adjuvant for use with a chemical used in agriculture comprising:
   from 15 to 35% by weight of one or more alkyl esters of fatty acids;
   from 5 to 25% by weight of one or more ammonium salts of inorganic anions selected from ammonium sulfate, ammonium phosphate and mixtures thereof;
   from 1 to 10% of a mixture of two or more cationic emulsifiers selected from the group consisting of fatty quaternary ammonium chlorides, fatty amine oxides, fatty alkyldimethylamine salts of simple organic acids and mixtures thereof; and
   from 1 to 30% of one or more other components to improve the form of the composition selected from alkyl polysaccharides, sorbate emulsifiers, fatty alkanolamides, glycols and mixtures thereof;
   wherein the cationic emulsifier acts as a coupling agent between the alkyl esters of fatty acids and the ammonium salts to form a homogeneous liquid composition.

* * * * *